(12) United States Patent
Pado et al.

(10) Patent No.: US 7,925,455 B2
(45) Date of Patent: Apr. 12, 2011

(54) METHOD AND SYSTEM FOR THE DETERMINATION OF DAMAGE LOCATION

(75) Inventors: Lawrence E. Pado, Saint Charles, MO (US); James P. Dunne, Ballwin, MO (US); Jeong-Beom Ihn, Bellevue, WA (US)

(73) Assignee: The Boeing Company, Chicago, IL (US)

( * ) Notice: Subject to any disclaimer, the term of this patent is extended or adjusted under 35 U.S.C. 154(b) by 62 days.

(21) Appl. No.: 12/018,888

(22) Filed: Jan. 24, 2008

(65) Prior Publication Data

US 2009/0192729 A1    Jul. 30, 2009

(51) Int. Cl.
   *G01B 5/28*       (2006.01)
   *G06F 19/00*      (2006.01)
(52) U.S. Cl. .......................................................... 702/36
(58) Field of Classification Search .................... 702/36, 702/33–35, 56; 73/570, 583, 802
   See application file for complete search history.

(56) References Cited

U.S. PATENT DOCUMENTS

| | | | |
|---|---|---|---|
| 6,006,163 A * | 12/1999 | Lichtenwalner et al. | 702/36 |
| 7,426,447 B2 | 9/2008 | Pado | |
| 2005/0075846 A1 * | 4/2005 | Kim | 703/1 |
| 2007/0260425 A1 * | 11/2007 | Kim | 702/182 |
| 2007/0260427 A1 * | 11/2007 | Kim | 702/185 |
| 2007/0265806 A1 * | 11/2007 | Kim | 702/187 |
| 2007/0265808 A1 * | 11/2007 | Kim | 702/188 |
| 2009/0099790 A1 * | 4/2009 | Pado | 702/35 |
| 2009/0182515 A1 * | 7/2009 | Pado et al. | 702/36 |

* cited by examiner

*Primary Examiner* — Cindy Hien-Dieu Khuu
(74) *Attorney, Agent, or Firm* — McNees Wallace & Nurick, LLC

(57) ABSTRACT

A method for determining the health of a structural element. The method includes providing a plurality of transducer elements arranged and disposed to permit measurement of vibration generated by at least one of the transducer elements at one or more of the other transducers elements. Vibration is induced with at least one transducer element. Vibration is measured at least one other transducer element, where the measured vibration corresponding to a vibratory path. At least one damage index value is calculated for each vibratory path in response to the measured vibration. At least one damage image is generated in response to the damage index value. The damage image assigns damage index values to each vibratory path. A damage location is determined from the damage image.

13 Claims, 7 Drawing Sheets

METHOD AND SYSTEM FOR THE DETERMINATION OF DAMAGE LOCATION

FIELD OF THE DISCLOSURE

The present disclosure is directed to a system and method for monitoring the integrity of structural bodies. In particular, the disclosure is directed to a system and method using transducer arrays and data analysis to detect, locate and characterize damage to a structure body.

BACKGROUND

Currently, inspection for damage to aircraft composite structures due to fatigue or impacts must be performed on a fixed schedule. These inspections are done to assess the integrity of the structure in question. Each inspection is time-consuming and is costly, not only in terms of time and skill needed to perform a thorough job, but also in terms of lost revenue from the aircraft being out of service. An automated onboard system for detecting and characterizing damage can eliminate this cost, except when significant damage has actually occurred. In addition, because the damage has been located and/or characterized (e.g., determination of damage size, depth, etc.), repairs can be performed more quickly by using the appropriate repair kits.

What is needed is a system and method that allows the assessment of the integrity of a structural body in real-time or near real-time wherein the location and the characteristics of any damage present can be determined.

SUMMARY

A first aspect of the present invention includes a method for determining the health of a structural element. The method includes providing a plurality of transducer elements arranged and disposed to permit measurement of vibration generated by at least one of the transducer elements at one or more of the other transducers elements. Vibration is induced with at least one transducer element. Vibration is measured by reading the induced voltage with at least one other transducer element, where the measured vibration corresponds to a vibratory path between the transducer that induced the vibration and the transducer that read the voltage caused by the vibration. At least one damage index value is calculated for each vibratory path in response to the measured vibration. At least one damage image is generated in response to the damage index value. The damage image assigns damage index values to each vibratory path. A damage location is determined from the damage image.

Another aspect of the present invention includes a structural health monitoring system having a plurality of transducer elements arranged and disposed to measure vibration generated by at least one of the transducer elements at one or more of the other transducers elements, the measurement taking place over vibratory paths between the transducer element generating the vibration and the transducer element measuring the vibration. The system also includes a controller element in communication with the plurality of transducer elements. The controller element is capable of analyzing data from the transducer elements and calculating at least one damage index value from the data for each vibratory path. The controller element also generates images from the damage index value and assigns damage index values to each of the vibratory paths. The controller element is further capable of determining a damage location from the damage image.

Still another aspect of the present disclosure is a vehicle having a structural health monitoring system. The vehicle includes a structural element and a plurality of transducer elements affixed to the structural element. The plurality of transducer elements are arranged and disposed to measure vibration generated by at least one of the transducer elements at one or more of the other transducers elements, the measurement taken place over vibratory paths between the transducer element generating the vibration and the transducer element measuring the vibration. The vehicle also includes a controller element in communication with the plurality of transducer elements. The controller element is capable of analyzing data from the transducer elements and calculating at least one damage index value from the data for each vibratory path. The controller element also generates images from the damage index value and assigns damage index values to each of the vibratory paths. The controller element is further capable of determining a damage location from the damage image.

An advantage of an embodiment of the present disclosure is that the system is an apparatus capable of providing and processing data useable in the determination of structural damage and the characterization of that damage. Specifically, the disclosure includes a system of transducers arranged on an aircraft or other structural component to monitor the health of the structure and to provide information about damage to a structure.

Other features and advantages of the present invention will be apparent from the following more detailed description of the preferred embodiment, taken in conjunction with the accompanying drawings which illustrate, by way of example, the principles of the invention.

BRIEF DESCRIPTION OF THE DRAWINGS

Wherever possible, the same reference numbers will be used throughout the drawings to refer to the same or like parts.

DETAILED DESCRIPTION OF THE INVENTION

Figure 1:
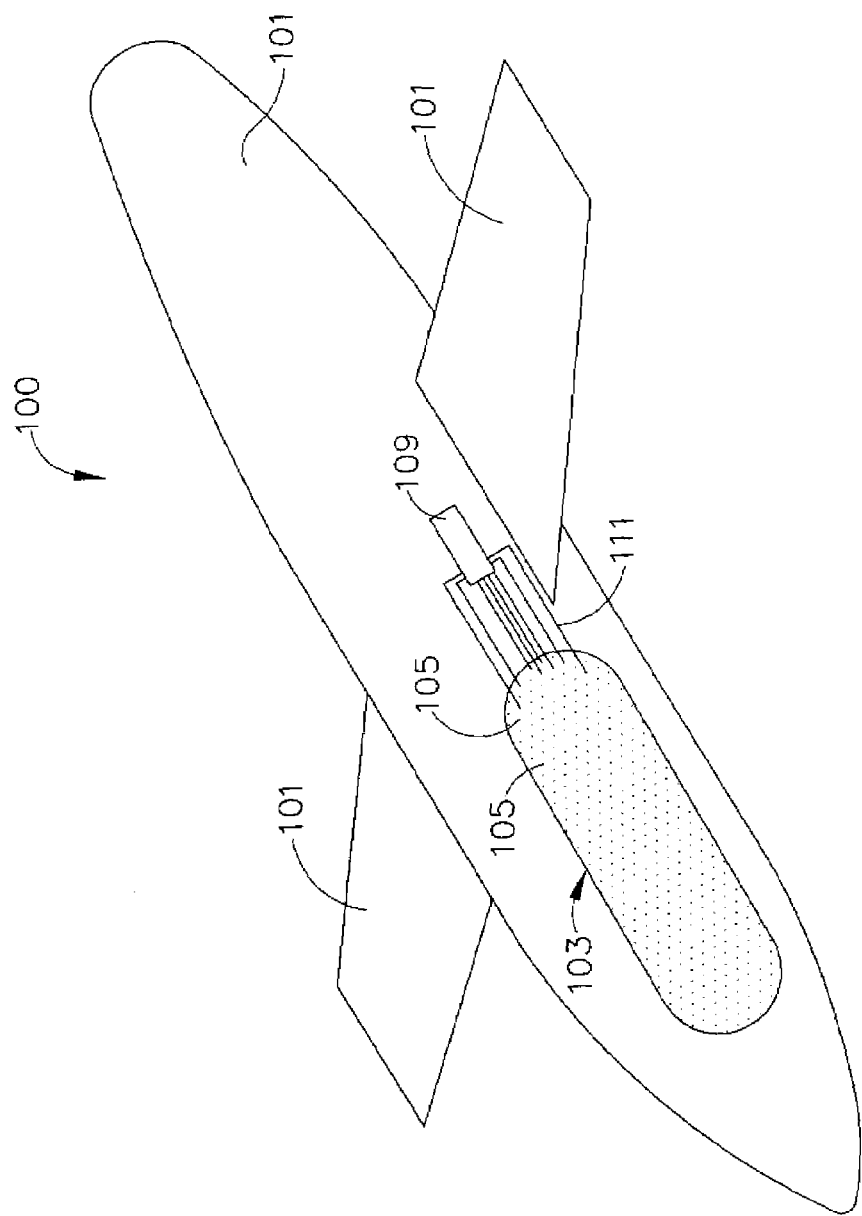
FIG. 1 shows perspective view of a vehicle with a cutaway view of a transducer array according to an embodiment of the present invention.

FIG. 1 shows a vehicle 100 according to an embodiment of the disclosure. The vehicle 100 may be an aircraft, a ground vehicle, a naval vessel or any other vehicle requiring structural health monitoring. The vehicle 100 includes a structural element 101, which may include, but is not limited to, a fuselage, door, panel, wing, engine component, or any other component that is susceptible to damage. The vehicle 100 includes a structural health monitoring array 103 made up of a plurality of transducer elements 105 arranged along a surface of the structural element 101. The transducer elements 105 are in electrical communication with a controller element 109 via signal wires 111 (examples of which are shown as broken lines in FIG. 1). The controller element 109 may be electrically connected to the transducer elements 105 in any suitable manner known in the art, including by conductive wires, wireless communication methods or any other method that permits the transmission of signals and/or data between the transducer element 105 and the controller element 109. The controller element 109 provides signals to and obtains data from transducers 105 to perform the health monitoring of the structural element 101. "Health monitoring", "structural health" and other uses of the term "health", as used herein refer to the structural integrity of a structure, component or equipment element. For example, damage to a surface or structure may include indentation, delamination (localized or otherwise), scratches, or any other damage caused by material fatigue, operation, foreign object impact or other mechanical imperfections present in the structure. In addition, damage may include a reduction in the integrity of the structure that may require analysis and/or potential repair. The array 103 includes transducer elements 105 affixed to the structural element 101. The structural element 101 may include any material or combination of materials typically present in a conventional vehicle 100 or structure construction. For example, the structural element 101 may include metal, composite, polymer, ceramic or any other material typically utilized for construction of vehicles 100 or other structures. The transducer elements 105 are preferably devices capable of both inducing a vibration of the structural element 101 and measuring vibration present in an attached structure. For example, the transducer element 105 may be, but is not limited to a piezoelectric transducer (PZT). In one embodiment, the transducer element 105 is a PZT and a voltage is provided to the PZT to induce motion and/or vibration. Vibration generated by the PZT is measured with surrounding transducer elements 105. For example, when a voltage is applied to a ceramic PZT transducer, the transducer expands thereby creating a vibration. Conversely, if a PZT is mechanically flexed (i.e., by a vibration) the transducer will generate a voltage proportional to that vibration which can then be read. By "vibration", "vibrating", "vibratory motion" and grammatical variations thereof, as used herein, it is meant to include reciprocal or non-reciprocal motions and/or strain within a material that are capable of being sensed and/or measured at a distance across a material. The controller element 109 is a microprocessor, integrated circuit or other device capable of controlling transducer elements 105 and collecting and/or analyzing data provided by the transducer elements 105.

The transducer elements 105 are affixed to the structural element 101 in any suitable manner that permits the generation of vibration in the structural element 101 by transducer elements 105 and the measurement of vibration of the transducer elements 105. In one embodiment, while not so limited, the transducer elements 105 are affixed directly to a structural element 101 by an adhesive. The transducer elements 105 may also be attached through embedding PZTs within the composite or sintering direct-write PZT solution to the surface.

Although FIG. 1 illustrates a vehicle 100, the present disclosure is not limited to a vehicle 100 and may include any structural element, including fixed structures, such as buildings, architectural elements, bridges or other structures.

Figure 2:
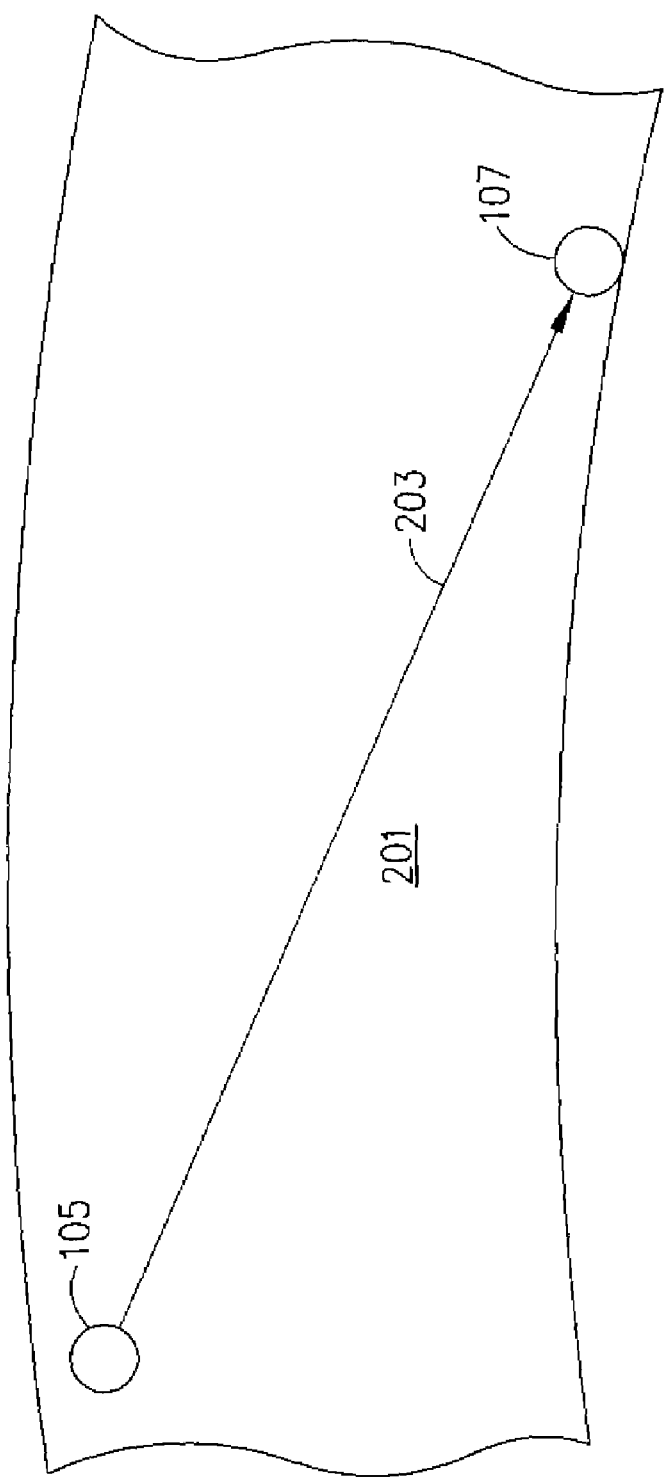
FIG. 2 shows a schematic view of a transducer array according to an embodiment of the present disclosure.

FIG. 2 shows a schematic illustration of a single vibratory path 203 arrangement between a transducer element 105 and a transducer element 107. As discussed above with respect to FIG. 1, the transducer elements 105 and transducer element 107 are affixed or otherwise applied to a substrate 201, such as a structural element 101 of a vehicle 100. The transducer elements 105 is activated, such as by providing a voltage or waveform voltage to the transducer elements 105. In response to the applied voltage, the transducer element 105 induces a vibration. The vibration propagates across the substrate 201 forming a vibratory path 203. Although the vibratory path 203 is illustrated as a single straight line, it is noted that the vibration generated by the transducer elements 105 propagates in all directions from transducer elements 105 along the substrate 201. The vibratory path 203 presents the approximate line between the source of the vibration and the point at which the vibration is measured. Sensor 107 senses and measures vibration and/or movement corresponding to the vibration propagating along vibratory path 203. The vibratory path 203 has altered vibration characteristics when passing through a damaged portion. Therefore, changes in the vibratory characteristics over an area of the substrate 203 may be utilized to determine if damage exists over the distance of the vibratory path. Sensor 107 may, for example, generate a voltage in response to vibration. The voltage or a signal corresponding to the voltage can be transmitted to a controller element 109 for collection and analyzing.

Figures 3, 4:
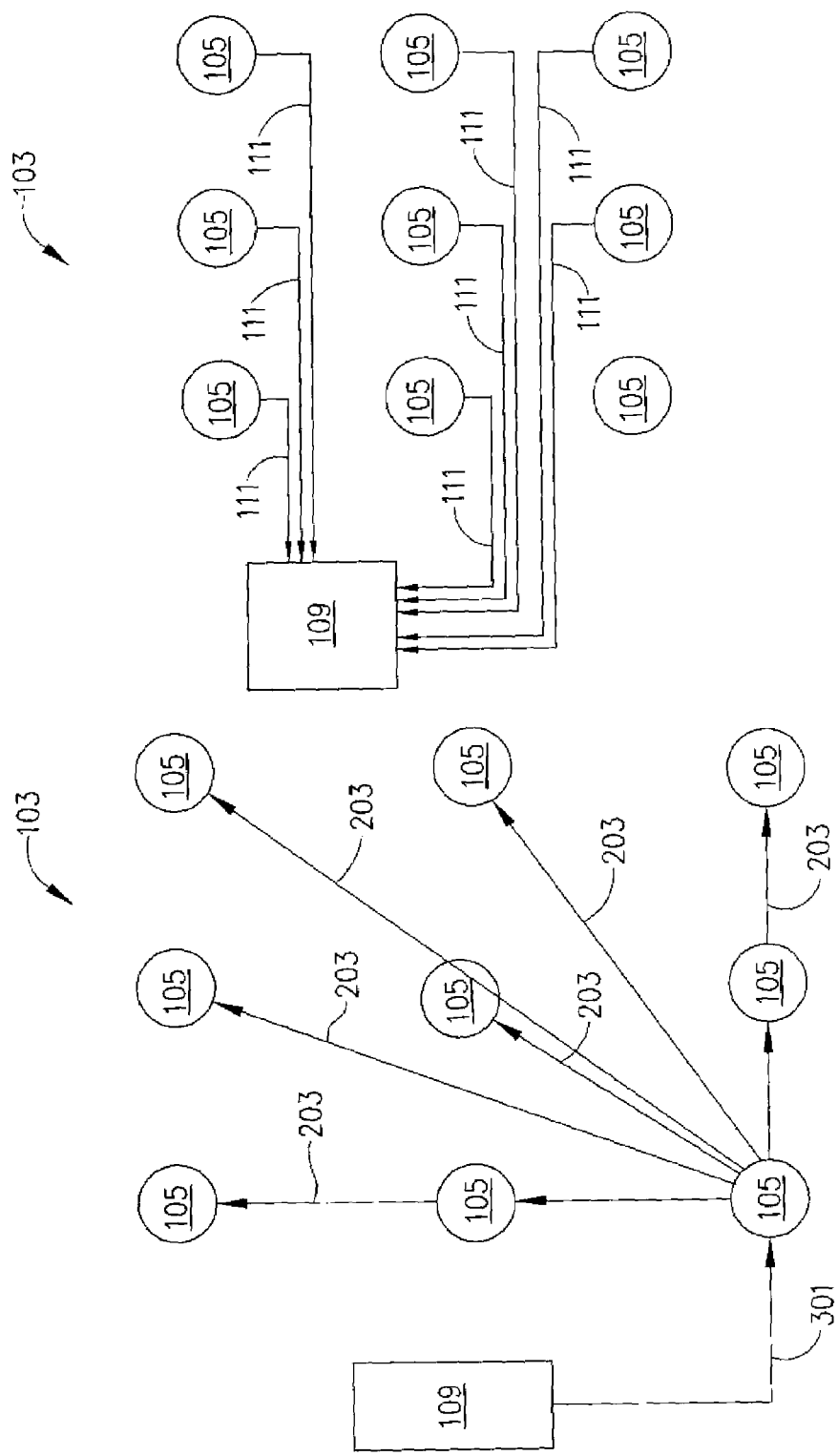
FIGS. 3-6 show a structural health monitoring arrays during a monitoring cycle according to an embodiment of the present disclosure.
Figure 6:
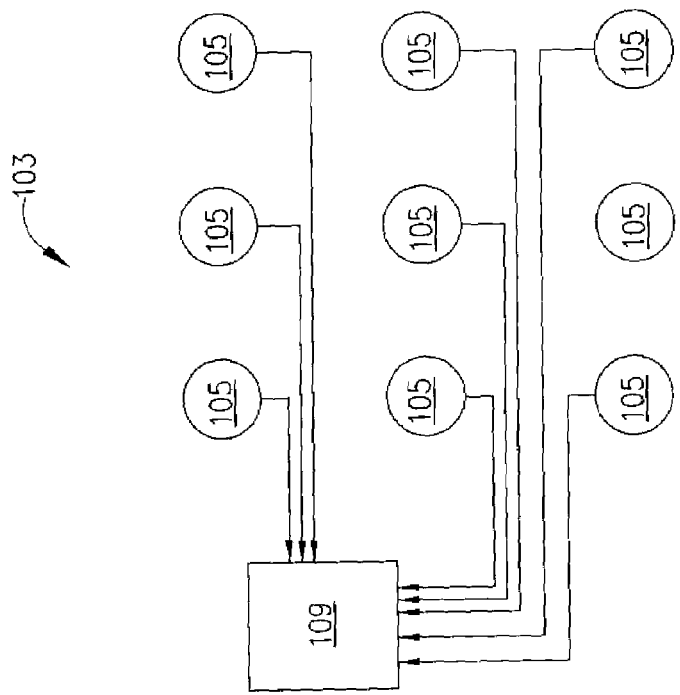

FIGS. 3-6 show a structural health monitoring array 103 during a monitoring cycle according to an embodiment of the present disclosure. The transducer elements 105 may be placed in any configuration along the structural element 101 or substrate 201. In one embodiment, the transducer elements 105 may be deposited on an interior surface of a vehicle, wherein the exposure to damage is primarily on an exterior surface. As shown in FIG. 3, a signal 301 from controller element 109 is sent to activate a transducer element 105. The signal may be a voltage, waveform or other signal that may be used by the transducer elements 105 to generate vibration. In response, the transducer element 105 generates a vibration that propagates along vibratory paths 203. The vibratory paths 203 travel across the substrate 201 and are measured by other transducer elements 105. As shown in FIG. 4, the measured values for vibration (e.g., voltages produced by the PZT) are transmitted to the controller element 109. Although FIGS. 3-6 show a total of eight transducer elements 105 and seven transducer elements 105 capable of measuring vibration from a single activated transducer element 105, the number of transducer elements 105 utilized to measure vibration may be any number of transducer elements 105 desired to provide paths (see e.g., FIG. 7) sufficient to determine the presence, location and characteristics of damage. In particular, in one embodiment, the vibration is converted to an electrical voltage by seven PZT transducer elements 105. As shown in FIG. 4, the seven transducer elements 105 measuring the vibration transmit the measured vibration to the controller element 109 and the controller element 109 collects and analyzes the vibration values.

Figure 5:
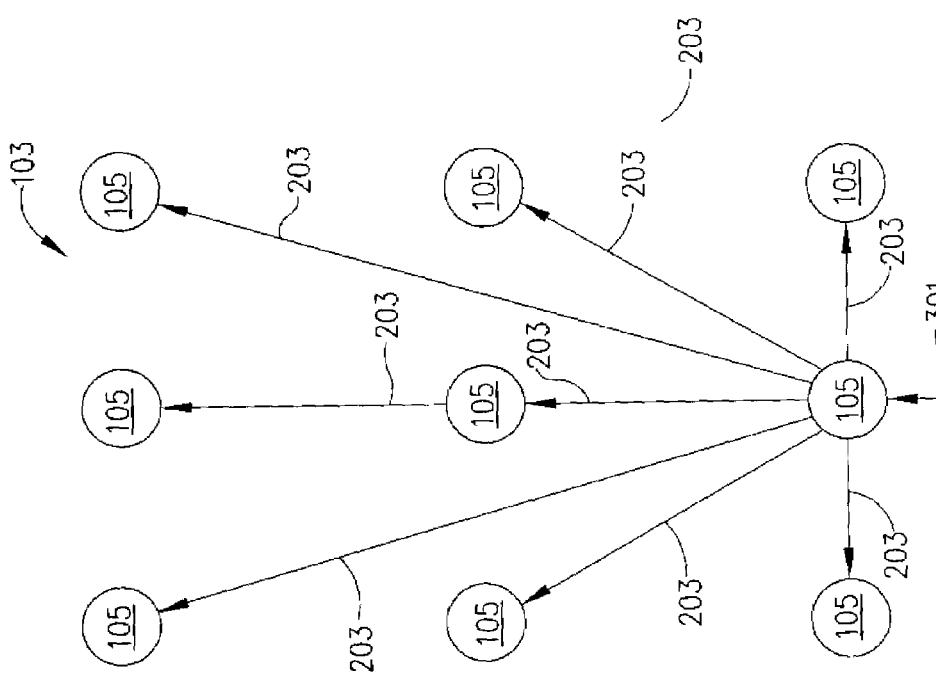
Figure 7:
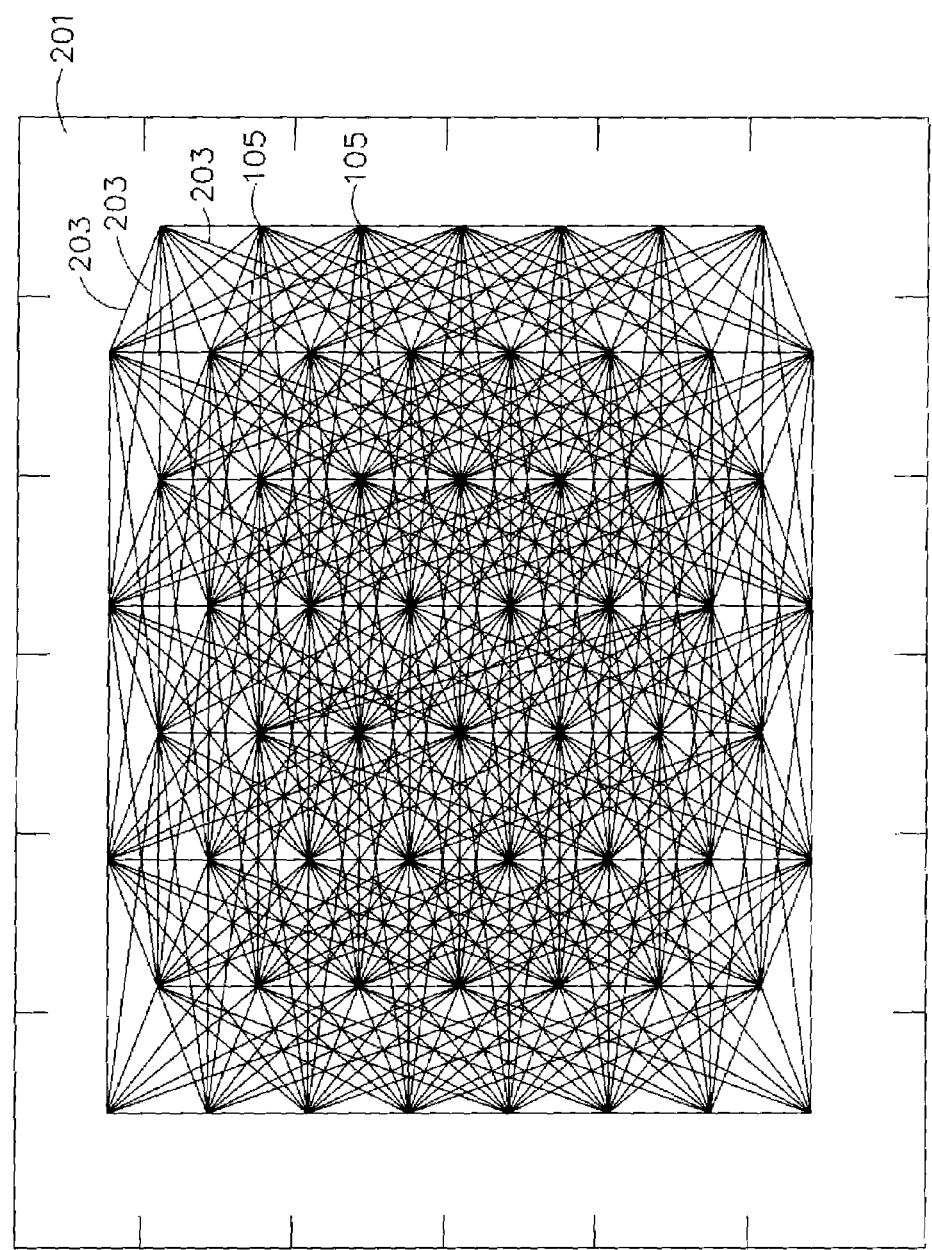
FIG. 7 shows a transducer array including vibratory paths according to an embodiment of the present disclosure.

The process is repeated as shown in FIG. 5, wherein a signal 301 is provided by the controller element 109 to another transducer element 105 different than the transducer element 105 in FIG. 3. In response, the transducer element 105 generates a vibration that propagates along vibratory paths 203. The vibratory paths travel across the substrate 201 and are measured by other transducer elements 105. As shown in FIG. 4, the measured values for vibration (e.g., voltages produced by the PZT) are transmitted to the controller element 109. The process continues to repeat until the desired number of vibratory paths 203 are measured. FIG. 7 shows an example of a network of vibratory paths 203 that may be measured over the area of a substrate 201.

In one embodiment, the controller element 109 compares the voltages transmitted by the PZT transducer elements 105 to a stored set of data corresponding to an undamaged substrate 201. If the substrate 201 is substantially undamaged, the voltages measured and the voltages stored are substantially the same and the resultant damage index (DI) value is zero or about zero. However, if damage is present, vibratory paths 203 passing through damage will measure a level of vibration different than the vibration propagating along vibratory path 203 measured on an undamaged substrate and therefore can characterize and locate the damage.

The system of the present disclosure includes an array of transducers 105 bonded to a structure that are then sequentially excited to produce a vibration that is then measured by the other transducers 105. Typically, thousands of vibratory signals are produced and recorded by the controller elements 109. Signals (i.e., vibrations) recorded when the structure is in a known 'good' state (i.e., undamaged state) are referred to as a reference signals. Alternatively, the controller element 109 may be programmed with, or otherwise contain historic or desired reference values. Signals recorded when the structure is in an unknown state are referred to as a comparison signal. Comparison signals may be generated, for example, during operation of vehicle 100 or during a maintenance cycle. Subtracting the reference and comparison signals and finding differences can then indicate damage, its location, and its characteristics. For example, wherein no difference in the reference and comparison signals exists, the conclusion that no damage is present may be made.

An excitation broadcast (i.e., induced vibration) from one activated transducer elements 105 and received by another transducer elements 105 is called a vibratory path 203. For example, the difference in the signal along a vibratory path 203 before and after an impact can be characterized by various techniques, and each technique has as an output called a "Damage Index" (DI). For any given structure there may be hundreds or thousands of total vibratory paths 203 as shown in FIG. 7, each having a DI, or multiple DI's (e.g., various DI's from different calculation techniques), corresponding to each vibratory path 203.

Figure 8:
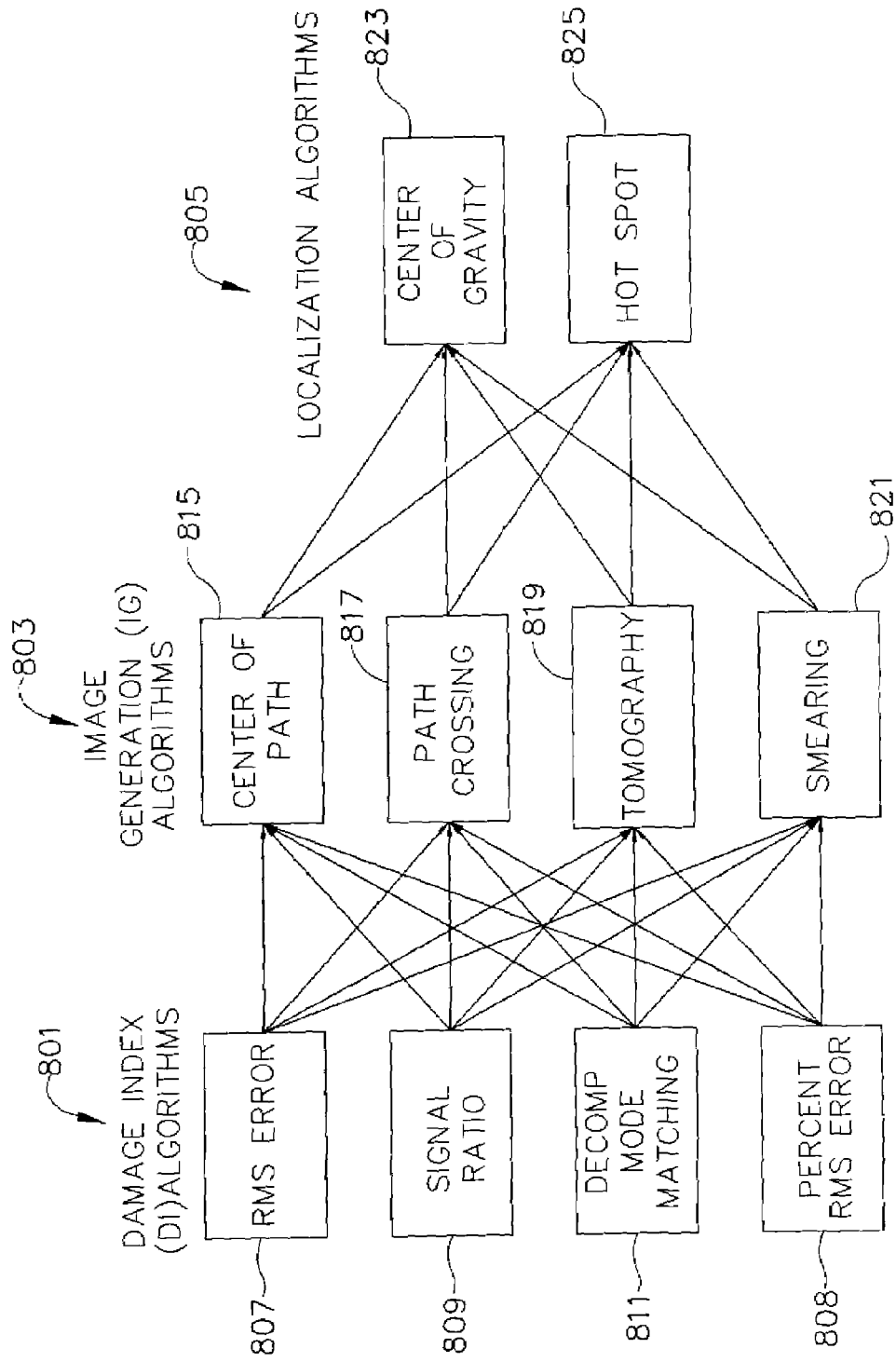
FIG. 8 shows a flow chart of the data analysis according to an embodiment of the present disclosure.

As shown in FIG. 8, one embodiment of the disclosure includes calculating four DI types (DI) according to the various Damage Index Algorithms 801. Each of the DI values is utilized to generate an image according to the Image Generation (IG) Algorithms 803. Once the images are produced, the images and DI's are utilized to determine the location of the damage using Localization Algorithms.

DI's determined by the present disclosure are calculated by four independent algorithms. As shown in FIG. 8, each algorithm corresponds to a DI-type. Specifically, the DI-types calculated include Root Mean Square Damage Index (RMS) Error ($DI_{RMSERROR}$) 807, Percent RMS Error Damage Index ($DI_{PercRMSErr}$) 808, Signal Ratio Damage Index ($DI_{SR}$) 809, and Signal Decomposition Damage Index 811.

The first DI-type is RMS Error DI ($DI_{RMSERROR}$) 807. RMS Error Damage Index is the root mean square of the difference between the response or measured vibration of a vibratory path 203 and a reference or stored signal. The $DI_{RMSERROR}$, also referred herein as $DI_{RMSERR}$, may be calculated according to the following formula:

$$DI_{RMSErr} = RMS(Response_{ref} - Response_{cmp})$$

$Response_{ref}$ is the signal stored corresponding to an undamaged structure or other desired reference value. $Response_{cmp}$ is the measured signal (e.g., voltage induced at transducer elements 105 by vibration of vibratory path 203) during structural health monitoring. The root mean square is taken for the particular vibratory path 203. The value of the $DI_{RMSERR}$ is then capable of being used to generate a damage image.

The second DI-type is Percent RMS Error DI ($DI_{PercRMSErr}$) 808. Percent RMS Error Damage Index is the RMS of the difference between the response or measured vibration of a vibratory path 203 and a reference or stored signal divided by the RMS value of the reference signal. The $DI_{PercRMSErr}$ may be calculated according to the following formula:

$$DI_{PercRMSErr} = \frac{RMS(Respsonse_{ref} - Response_{cmp})}{RMS(Response_{ref})}$$

$Response_{ref}$ and $Response_{cmp}$ are as defined above in the discussion of the RMS Error DI 807. The value of the $DI_{PercRMSErr}$ 808 is then capable of being used to generate a damage image.

The third DI-type is a Signal Ratio DI ($DI_{SR}$) 809. The signal ratio Damage Index is the RMS of the response or measured value of the vibration of a vibratory path 203 divided by the RMS of a reference or stored signal. Lamb Mode Isolation (LMI) may be utilized to isolate a single mode for calculation of $DI_{SR}$. When the structure is excited at a certain frequency, Lamb waves are generated that travel through the structural element 101. At any given frequency, there are multiple lamb wave modes that are excited, and thus the response that is recorded is a superposition of all of the excited modes. These Lamb wave modes travel at different velocities, and so in simple structures and at certain frequencies these modes may be distinguished and/or isolated in the response based on the time of flight from the exciting transducer to the receiving transducer (i.e., the vibratory path 203). For example, while not so limited, the $A_0$ mode may be used as an exemplary mode for the calculation of $DI_{SR}$. The timing may be calculated using Finite Element Analysis. It is noted, however, that other methods may be also be utilized to a mode. The $DI_{SR}$ may be calculated according to the following formula:

$$DI_{SR} = RMS(Response_{cmp})/RMS(Response_{ref})$$

$Response_{ref}$ and $Response_{cmp}$ are as defined above in the discussion of the RMS Error DI. The value of the $DI_{SR}$ is then capable of being used to generate a damage image.

The fourth DI-type is Signal Decomposition DI Algorithm 811. Decomposition as used herein is defined as the process of converting a complex signal into a sum of simpler signals. One embodiment includes decomposing the signal measured at the transducer elements 105 into a sum of shifted and scaled versions of the input signal at the activated transducer elements 105. The decomposition is accomplished by cross correlating the input and output signals. At the point (shift) of greatest correlation, the sensor signal is divided by the input signal to obtain the scaling factor. The shifted and scaled input signal (i.e., at the activated transducer elements 105) is then subtracted from the measuring transducer signal and the process is repeated until a given threshold is reached or a fixed number of decomposition signals have been produced.

The reference signal is decomposed into twenty shifted and scaled versions (Ref, iRef) of itself that when recombined, recreate the reference signal (Ref). The comparison signal is decomposed into twenty shifted and scaled versions (Cmp, iCmp) of itself that when recombined recreate the comparison signal (Cmp).

A matrix (e.g., a 20×20 array) is generated such that each element Matrix (iRef, iCmp) holds a binary number of 0 if the shifting of Refi, Ref does not match the shifting of Cmp, iCmp, and 1 if it does match. The elements in the array are then summed. The total is provided as numMatches. The Signal Decomposition DI 811 may be calculated according to the following formula:

Signal Decomposition Final $DI_{1-3}$=numMatches

As shown in FIG. 8, once a vibratory path 203 has been assigned a DI (i.e., a value for DI under each of the desired DI-types), Image Generation algorithms 803 may be used to provide two dimensional maps of the damage severity. For example, a color coding or other indicia may be assigned to increasing values of DI. Therefore, maps may show damage severity on a two dimensional map.

A set of images is generated for each of the types of DI. In one embodiment, four image generation algorithms include the Center of Path Image 815, Path Crossing Image 817, Tomography Image 819, and Smearing Image 821. In the exemplary embodiment, the combinations of DI algorithms and IG algorithms for a vibratory path 203 or intersecting vibratory paths 203 will create a total of twenty images. For example, in one embodiment, this image generation technique may be applied to form an image that has a resolution of 0.25" per pixel. Accordingly, an exemplary structure measuring 10' by 10' may have an image resolution of 40 by 40 pixels. It is to be understood that pixel resolution having different sizes may be used.

The first image generation type includes a Center Path Image 815. The Center Path Image assigns the value of the DI to the center of the vibratory path.

The second generation type includes a Path Crossing Image 817, where the value of the DI is assigned to the entire vibratory path 203 and any points wherein vibratory paths 203 intersect, an image value corresponding to the sum of the DI's at the intersection of the vibratory paths 203.

Figure 9:
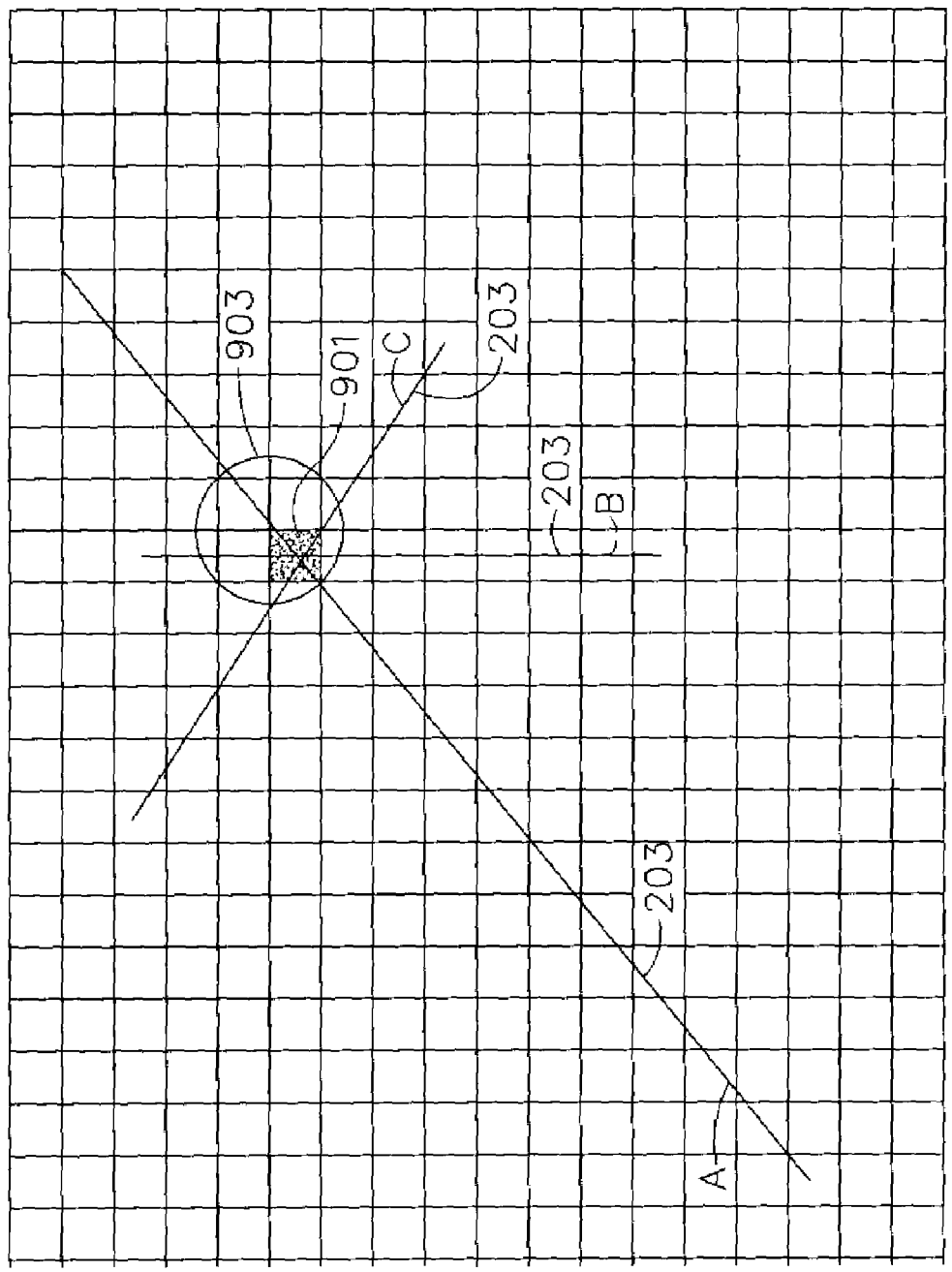
FIG. 9 shows an intersection of vibratory paths at a damaged portion of the structural element according to an embodiment of the present disclosure.

The third image generation type includes Tomography Image 819. Tomography includes a method in which portions of the total DI value are assigned to corresponding portion of the vibratory path 203. For example the different portions of a path may be represented as an area 901 of a grid that the path goes though (as shown in FIG. 9). The area 901 is shown as a square, but other geometries may also be used. For instance, if the area 901 that the vibratory path 203 passes through does not contain damage, none or very little of the DI value of the line should be assigned to area 901. If however, the vibratory path 203 passes though an area 901 that contains damage 903, the area 901 in the location of damage will be assigned all or a large proportion of the DI cost. Since many of the areas 901 will have multiple vibratory paths 203 passing through them, the value of these areas 901 can be found by solving a set of n equations for n unknowns. If the areas 901 are square pixels, then once the values of each area 901 has been calculated, a tomographic image may be generated.

The fourth type of image generation includes Smearing Image 821. Smearing is a linear interpolation of the values of DI assigned to the center of the vibratory path 203.

As shown in FIG. 8, after the images are created, Localization Algorithms 805 may be applied to determine the location of the damage. The localization algorithms include Hot Spot Localization 825, and Center of Gravity Localization 823. For example, since there are twenty images and two location algorithms there may be 40 estimates of damage location. It is to be understood that additional image DI and localization algorithms will increase the number of estimates of damage location.

The first localization technique includes Hot Spot Localization 825, wherein the location of damage is estimated to be at the location of the pixel with the highest DI value (i.e., a point on the two dimensional map generated in the image generation step). That is, the point on the map generated in the image generation step having the highest DI value or sum of DI's depending on the DI-type and image generated.

The second localization technique is Center of Gravity Localization 823. The Center of Gravity is calculated by taking an average of the masses multiplied by their distances from a reference point. The calculation is done for the x-axis ($X_{cg}$) and the y-axis ($Y_{cg}$). For example, Center of Gravity can be calculated according to the following formula with a reference point taken at (0,0) and N paths:

$$X_{CG} = \frac{\sum_{i=1}^{N} x_i \cdot m_i}{M_{TotalMass}}$$

$$Y_{CG} = \frac{\sum_{i=1}^{N} y_i \cdot m_i}{M_{TotalMass}}$$

$$M_{TotalMass} = \sum_{i=1}^{N} m_i$$

wherein $m_i$ is the DI value of path i and N is the total number of paths. $X_i$ is the x location of the of the center of path i and $y_i$ is the y location of the center of path i. Xcg is the estimated X location of the damage and Ycg is the estimated Y location of the damage.

From a set of known damage locations created from multiple impacts, a multiple linear regression model is created using the 40 estimated locations. This model will fuse together the 40 damage location estimates into a single higher accuracy estimate. In our case, the accuracy was twice as good as the best single estimate from the 40 possibilities base on the error magnitude. While not wishing to be bound by theory, it is believed that the accuracy will always be at least as good as the best single estimate.

(DI1,IG1,L1),(DI1,IG1,L2),(DI1,IG2,L1),(DI1,IG2,L2), . . .

(DI2,IG1,L1),(DI2,IG1,L2),(DI2,IG2,L1),(DI2,IG2,L2), . . .

(DI3,IG1,L1),(DI3,IG1,L2),(DI3,IG2,L1),(DI3,IG2,L2), . . .

(DI4,IG1,L1),(DI4,IG1,L2),(DI4,IG2,L1),(DI4,IG2,L2), . . .

The array created shows DI[DI-type number], IG[IG type number] and L[Localization type number]. This array includes D1 to D5, IG1 to IG4 and L1 to L2. The damage is then assigned to the x and y positions and the damage location is determined.

In addition, linear regression may be calculated on the array to further fuse the multiple data points. The following equation is solved using linear regression:

$$X_{Estimated} = A_o + A_1 X_1 + \ldots + A_{40} X_{40}$$

wherein $X_{Estimated}$ is the dependent variable. When forming the model (solving for the As), $X_{Estimated}$ is the true measured X location of the damage center. After the model is formed, it is the fused estimated X location of the damage center. $X_1$ through $X_{40}$ are the forty X locations from the forty algorithms. These are the independent variables. $X_1$ (for example) would come from (DI1,IG1,L1). $A_0$ through $A_{40}$ are the constants that are solved. As long as there are at least 41 impacts, this equation can be solved with any known linear regression tool. Thus the 40 estimates are 'fused' together to get a final, more accurate location. The Y location may be solved utilizing the same method as utilized to solve X.

EXAMPLE

In this example an array of PZT transducer elements 105 is bonded to the internal surface of an aircraft structure. Each transducer element 105 is identified by an integer number from N=1 to n. Each of these transducer elements 105 has an assigned location (x,y). Although the spacing of the transducer elements 105 may vary greatly one example, includes a 3" spacing grid. The total number of transducer elements 107 is a function of the size of the structural element 101 being monitored.

Starting with transducer N=1, the transducer is activated with a logarithmic chirp signal from 50 Khz to 600 Khz at a sample rate of 2.7 Mhz. At each of the other (n−1) transducers, the vibration received is measured and the measurement is transmitted to the controller. Each signal includes 1024 recorded data points. 1024 points of data are recorded at each transducer element 105 each time a transducer is excited. In one example, 301 transducers are in the array and one of them is excited with the other 300 recording 1024 points of data.

The above steps are repeated until all transducers have acted as an actuator (i.e., activated transducer elements 105). A total of n*(n−1) signals are created, each of which is referred to as a vibratory path 203. Each of these signals is considered a reference or baseline signal, since the part is in a known 'good' or undamaged state.

When it is desired to monitor the structure health of the aircraft, the process steps above are repeated. The above steps are repeated to obtain comparison signals (e.g., Response$_{cmp}$) to compare to the baseline signals (e.g., Response$_{ref}$).

For each recorded reference and comparison signal of a vibratory path 203, a Damage Index or DI is calculated. In one embodiment of this disclosure there are four types of DIs that may be calculated. The four types include RMS Error DI Algorithm, Percent RMS Error DI Algorithm, Signal Ratio DI Algorithm, and Decomposition Algorithm. In one example all of the four DI types are calculated.

An image is generated using the DI's, creating a set of images for each of the DIs types for each of the image generation algorithms. The four image generation algorithms are Center of Path Image, Path Crossing Image, Tomography Image, and Smearing Image. The image generation will create a total of twenty images. When the images are generated, in this example, the image has a resolution of 0.25" per pixel. Thus, a part measuring 10' by 10' with have a resolution of 40 by 40 pixels.

For each of the twenty images created, damage localization algorithms are applied using each of the two location algorithms. There are two location algorithms that are utilized in this example. The two location algorithms are Hot Spot Localization and Center of Gravity Localization. In example, there are twenty images and two location algorithms resulting in 40 estimates of damage location.

A multiple linear regression model is created using the 40 estimated locations. This regression model fuses together the 40 damage location estimates into a single higher accuracy estimate. The model created in above step is usable to provide the damage location estimate.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

The invention claimed is:

1. A method for determining the health of a structural element comprising:
   providing a plurality of transducer elements;
   inducing vibration with at least one transducer element of the plurality of transducer elements;
   measuring vibration with at least one other transducer element of the plurality of transducer elements, the measured vibration corresponding to at least one vibratory path;
   calculating two or more independent damage index values of different damage index types for each vibratory path of the at least one vibratory path in response to the measured vibration;
   generating two or more sets damage images, each set consisting of two or more damage images for each damage index type; wherein each of the two or more damage image sets correspond to each of the two or more damage index values; and
   determining a single damage location by processing the two or more images contained in the two or more sets of damage images by two or more location algorithms;
   wherein each independent damage index value of the two or more independent damage index values is created using different damage index algorithms on a single data sequence.

2. The method of claim 1, wherein calculating includes determining three or more damage index values for each vibratory path.

3. The method of claim 1, wherein the providing includes affixing the transducer elements to a structural element.

4. The method of claim 3, wherein the structural element is a portion of a vehicle or a fixed structure.

5. The method of claim 1, wherein each image of the two or more sets of damage images corresponds to each damage index, each image representing a same damage location.

6. A structural health monitoring system comprising:
   a plurality of transducer elements arranged and disposed to measure vibration generated by at least one of the transducer elements at one or more of the other transducers elements, the measurement taken place over vibratory paths between the transducer element generating the vibration and the transducer element measuring the vibration; and
   a controller element in communication with the plurality of transducer elements, the controller element capable of analyzing data from the transducer elements and calculating two or more independent damage index values of different damage index types from a single data sequence for each vibratory path, and further generating two or more sets of damage images for the damage index values, each set consisting of two or more damage images for each damage index type, the damage image assigning damage index values to vibratory paths, the controller element further being capable of determining a damage location from the two or more sets of damage images by two or more location algorithms;
   where each independent damage index value of the two or more independent damage index values is created using different damage index algorithms on the single data sequence.

7. The system of claim 6, wherein the transducer elements are arranged and disposed on a vehicle or a fixed structure.

8. The system of claim 6, wherein calculating includes determining three or more damage index values for each vibratory path.

9. The system of claim 6, wherein the determining includes determining an estimate of a damage location from the two or more sets of damage images wherein each estimate of damage location represents an estimate of a single damage location.

10. A vehicle having a structural health monitoring system, the vehicle comprising:
    a structural element;
    a plurality of transducer elements affixed to the structural element, the transducer elements being arranged and disposed to measure vibration generated by at least one of the transducer elements at one or more of the other transducers elements, the measurement taken place over vibratory paths between the transducer element generating the vibration and the transducer element measuring the vibration; and
    a controller element in communication with the plurality of transducer elements, the controller element capable of analyzing data from the transducer elements and calculating two or more independent damage index values of different damage index types from a single data sequence for each vibratory path, and further generating two or more sets of damage images from the two or more damage index values, each set consisting of two or more damage images for each damage index type; wherein each of the two or more damage image sets correspond to each of the two or more damage index values;
    the controller element capable of determining a damage location from the two or more sets of damage images by two or more location algorithms;
    wherein each independent damage index value of the two or more independent damage index values is created using different damage index algorithms on the single data sequence.

11. The vehicle of claim 10, wherein calculating includes determining three or more damage index values.

12. The vehicle of claim 10, wherein the structural element is fabricated from a material selected from the group consisting of metal, composite, polymer, ceramic and combinations thereof.

13. The vehicle of claim 10, wherein the vehicle is an aircraft.

* * * * *